(12) United States Patent
Ci

(10) Patent No.: US 10,701,964 B2
(45) Date of Patent: Jul. 7, 2020

(54) NUTRITIONAL COMPOSITION FOR TONIFYING SPLEEN AND METHOD FOR PREPARING THE SAME

(71) Applicant: Zhonghua Ci, Beijing (CN)

(72) Inventor: Zhonghua Ci, Beijing (CN)

( * ) Notice: Subject to any disclaimer, the term of this patent is extended or adjusted under 35 U.S.C. 154(b) by 292 days.

(21) Appl. No.: 15/958,951

(22) Filed: Apr. 20, 2018

(65) Prior Publication Data
US 2019/0159499 A1   May 30, 2019

(30) Foreign Application Priority Data

Nov. 30, 2017 (CN) .......................... 2017 1 12442232

(51) Int. Cl.
| | |
|---|---|
| *A23L 33/105* | (2016.01) |
| *A61K 36/48* | (2006.01) |
| *A61K 36/8994* | (2006.01) |
| *A61K 36/62* | (2006.01) |
| *A61K 36/076* | (2006.01) |
| *A61K 36/725* | (2006.01) |
| *A23L 7/17* | (2016.01) |
| *A23P 10/25* | (2016.01) |

(52) U.S. Cl.
CPC ............. *A23L 33/105* (2016.08); *A23L 7/17* (2016.08); *A23P 10/25* (2016.08); *A61K 36/076* (2013.01); *A61K 36/48* (2013.01); *A61K 36/62* (2013.01); *A61K 36/725* (2013.01); *A61K 36/8994* (2013.01); *A23V 2002/00* (2013.01); *A23V 2200/324* (2013.01); *A23V 2250/21* (2013.01); *A23V 2300/10* (2013.01); *A23V 2300/16* (2013.01)

(58) Field of Classification Search
CPC .. A61K 2300/00; A61K 36/076; A61K 36/48; A61K 36/62; A61K 36/725; A61K 36/8994; A61K 36/77; A61K 36/8967; A61K 36/899; A23V 2002/00; A23V 2250/21; A23V 2300/10; A23V 2200/324; A23V 2300/16; A23V 2200/30; A23V 2200/32; A23V 2300/14; A23V 2200/326; A23V 2300/38; A23V 2200/31; A23L 33/105; A23L 11/05; A23L 19/09; A23L 19/10; A23L 31/00; A23L 7/143; A23L 7/17; A23L 33/10; A23P 10/25
See application file for complete search history.

(56) References Cited

U.S. PATENT DOCUMENTS

2015/0037389 A1* 2/2015 Ragot .................... A61K 36/74
424/439

* cited by examiner

*Primary Examiner* — Aaron J Kosar
(74) *Attorney, Agent, or Firm* — Cantor Colburn LLP

(57) ABSTRACT

The present application discloses a nutritional composition for tonifying spleen. The nutritional composition includes the following components of raw materials in parts by weight: rice 50-90, soybean 8-23, *Semen coicis* 2-12, *Gorgon euryale* seed 3-12, *poria* 0.4-1.6, and Chinese date 0.3-1.5. The present disclosure, in view of the spleen's special susceptibility to dampness pathogen, complies with the physiological function characteristics of the spleen itself, provides the prescription with an assistant effect of restoring the spleen's function as a starting point, is suitable to cooperate with staple foods for long-term consumption and easily accepted by people due to the good taste, and can achieve certain efficacies of tonifying the spleen and removing dampness.

20 Claims, 1 Drawing Sheet

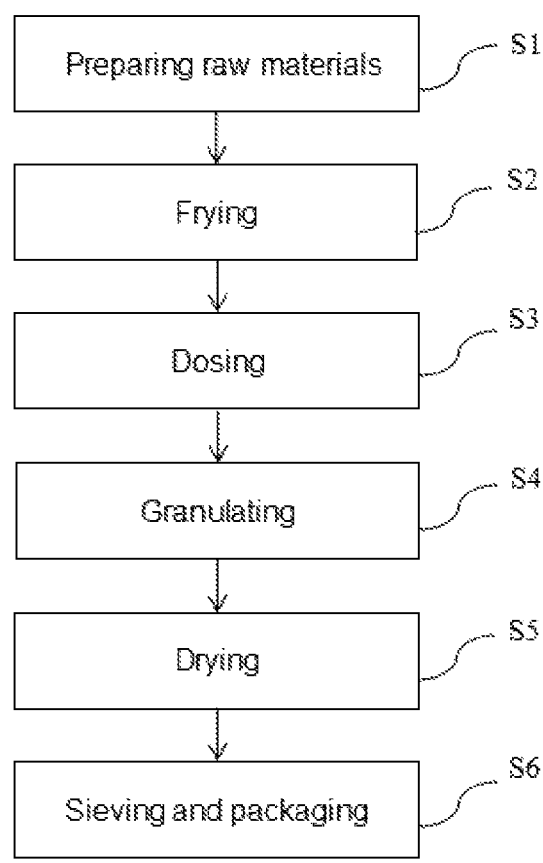

NUTRITIONAL COMPOSITION FOR TONIFYING SPLEEN AND METHOD FOR PREPARING THE SAME

TECHNICAL FIELD

The present disclosure belongs to the technical field of food processing, and particularly relates to a nutritional composition for tonifying spleen and a method for preparing the same.

BACKGROUND

In modern society, people have heavy dampness due to unhealthy living habits such as disordered eating, environmental pollution, overtime working, and late stay-up, with the body being in a sub-health status, and in serious cases, even high blood pressure, cardiovascular and cerebrovascular diseases, malignant tumor and so on are caused. In fact, all of these diseases are related to the spleen. There is an old saying as "it is easy to remove various types of coldness, but it is difficult to remove dampness, because dampness is sticky and turbid, as oil into flour." Due to the heavy dampness in the body, different populations develop symptoms such as fatigue, poor appetite, unshaped stool, dark yellow skin, fat accumulation, and weakness and edema, severely affecting people's physical and psychological health. The traditional cupping and scraping in the traditional Chinese medical science also can achieve the effects of tonifying the spleen and removing the dampness, but the effects usually are not lasting enough.

Taking coarse cereals has had thousands of years of history in our country, and the functions of refreshing, relieving tension, and prevention and health care can be achieved through dieting. With the increasingly emerging problem of "sub-health", the food therapy is more and more popular due to its advantages of being healthy and natural, moreover, with regard to problems easily arising, it is of critical significance to develop a health-care food having the efficacies of maintaining good health and tonifying the spleen by taking the cereals as a carrier, combining the precious experience of traditional Chinese health care and accumulation of good aspects of tonifying the spleen of the traditional Chinese medical science, and using technologies and methods of modern sciences, based on the homology between medicine and food.

Currently, similar health-care foods with the function of tonifying the spleen are already available in the market, but in most cases, the matching of different foods is chaotic, does not follow the pharmacology, and has relatively bad taste.

SUMMARY

A main object of the present disclosure is to provide a health-care food for tonifying spleen and removing dampness.

In order to achieve the above object, according to one aspect of the present disclosure, a nutritional composition for tonifying spleen is provided.

The nutritional composition for tonifying spleen according to the present disclosure includes the following components of raw materials in parts by weight: rice 50-90, soybean 8-23, Semen coicis 2-12, Gorgon euryale seed 3-12, poria 0.4-1.6, and Chinese date 0.3-1.5.

Furthermore, the nutritional composition for tonifying spleen includes the following components of raw materials in parts by weight: rice 60-80, soybean 10-20, Semen coicis 5-9, Gorgon euryale seed 4-8, poria 0.7-1.3, and Chinese date 0.6-1.2.

Furthermore, the nutritional composition for tonifying spleen includes the following components of raw materials in parts by weight: rice 70, soybean 15, Semen coicis 7, Gorgon euryale seed 6, poria 1, and Chinese date 1.

Furthermore, the nutritional composition for tonifying spleen further includes a Chinese herbal medicine extract of 1-3 parts, wherein the Chinese herbal medicine extract includes the following components of raw materials in parts by weight: *polygonatum odoratum* 12-30, dried longan pulp 13-24, dried orange peel 7-17, lily 17-26, Chinese yam 13-25, and hyacinth bean 13-28.

In order to achieve the above object, according to another aspect of the present disclosure, a method for processing a nutritional composition for tonifying spleen is further provided.

The method for processing a nutritional composition for tonifying spleen according to the present disclosure includes the following steps in sequence:

step 1, preparing raw materials: purifying and sorting rice, soybean, *semen coicis*, Gorgon euryale seed, poria, and Chinese date for subsequent use;

step 2, frying: frying respective components of raw materials under a condition of 100-200° C. for 25-120 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains;

step 5: drying: drying the mixed rice grains through a microwave dryer, wherein a water content of the material is kept below 12%, and cooling the dried mixed rice grains at a room temperature;

step 6: sieving and packaging: sieving the cooled mixed rice grains, and vacuum-packaging the sieved mixed rice grains.

Furthermore, temperatures of three phases of the double-screw extruder are kept at 60° C., 90-120° C., and 90° C., respectively.

Furthermore, a heating temperature of the microwave dryer is kept at 50-60° C.

Furthermore, in a dosing process of the step 3, a Chinese herbal medicine extract of 1-3 parts is further added, and the Chinese herbal medicine extract includes the following components of raw materials in parts by weight: *polygonatum odoratum* 12-30, dried longan pulp 13-24, dried orange peel 7-17, lily 17-26, Chinese yam 13-25, and hyacinth bean 13-28.

Furthermore, the Chinese herbal medicine extract is prepared through the following method:

drying and grinding respective raw materials into a medicinal powder, subjecting the medicinal powder to ultrasonic extraction, centrifugation, and concentration with an ethanol solution of 40-65% in volume percentage to obtain the Chinese herbal medicine extract.

Furthermore, in a process of preparing the Chinese herbal medicine extract, a vacuum dryer is used for drying, a temperature parameter is 75° C.-80° C., and a vacuum degree is between a negative pressure of 0.08 MPa and a negative pressure of 0.1 MPa.

The present disclosure, in view of the spleen's special susceptibility to dampness pathogen, complies with the physiological function characteristics of the spleen itself, provides the prescription with an assistant effect of restoring the spleen's function as a starting point, is suitable to cooperate with staple foods for long-term consumption, is easily accepted by people due to the good taste, and can achieve certain efficacies of tonifying the spleen and removing dampness.

BRIEF DESCRIPTION OF DRAWINGS

The FIGURE, constituting a portion of the present application, is used for further understanding of the present disclosure, so as to make it more obvious other features, objects, and advantages of the present application. Exemplary examples of the present disclosure, drawings, and description thereof are used to explain the present disclosure, rather than improperly limiting the present disclosure. In the FIGURE, FIG. 1 is a flow chart of a technology for processing a nutritional composition of examples of the present disclosure.

DETAILED DESCRIPTION OF EMBODIMENTS

In order to make a person skilled in the art better understand solutions of the present invention, below technical solutions of the examples of the present invention will be described clearly and completely in conjunction with FIGURE of the examples of the present invention. Apparently, some but not all of examples of the present invention are described. Based on the examples of the present invention, all the other examples, which a person ordinarily skilled in the art obtains without paying inventive effort, fall within the scope of protection of the present invention.

Besides, the term "include (comprise)" and any variants thereof are intended to cover non-exclusive containing, for example, a product including a series of raw materials or a method including a series of steps is not necessarily limited to listing those raw materials or steps, but may include other steps or raw materials which are not clearly listed or inherent to the method or product.

It should be indicated that examples of the present invention and features in the examples can be combined with each other without conflict. The present invention will be described in detail with reference to the FIGURES in conjunction with the examples.

In one aspect, the present disclosure provides a nutritional composition for tonifying spleen having such function, including the following components of raw materials in parts by weight: rice 50-90, soybean 8-23, *Semen coicis* 2-12, *Gorgon euryale* seed 3-12, *poria* 0.4-1.6, and Chinese date 0.3-1.5.

Rice: the traditional Chinese medical science holds that rice is sweet in taste and mild in nature, exerts the curative effect through the spleen, stomach, and lung channels, has the efficacies of nourishing the middle energizer and supplementing qi (vital energy), tonifying the spleen and nourishing the stomach, replenishing the essence and improving the memory, harmonizing the internal organs, promoting the blood circulation, improving the hearing and eyesight, eliminating annoyance, quenching thirst, and curing diarrhea, and it is believed that taking more rice can "strengthen the body and improve the look".

Soybean: soybean, mild in nature and sweet in taste, exerts the curative effect through the spleen and large intestine channels, tonifies the spleen and regulates the middle energizer, moisturizes dryness and eliminates ascites, clears away heat and toxic materials, supplements qi, and is used for treatment of heat accumulation in stomach, water distention swollen poison, and difficult urination.

*Semen coicis*: *semen coicis*, sweet and light in taste and slightly cold in nature, and non-toxic, exerts the curative effect through the spleen, stomach, lung, and large intestine channels, clears away heat and promotes diuresis, eliminates wind-dampness, promotes urination, invigorates the lung and discharges pus, tonifies the spleen and stomach, and strengthens the bones and muscles, and is used for treatment of rheumatism pain, dampness-heat beriberi, dampness arthralgia muscular constriction, dampness arthralgia, edema, pulmonary collapse and pulmonary abscess, cough with pus and blood, pharyngitis carbuncle, and intestinal carbuncle and heat strangury.

*Gorgon euryale* seed: *Gorgon euryale* seed, sweet and astringent in taste, and mild in nature, exerts the curative effect through the spleen and kidney channels, invigorates kidney to strengthen essence, nourishes spleen and cures diarrhea, dispels dampness and arrests leucorrhoea, and is used for treatment of gonobolia and spermatorrhea, enuresis and frequent urination, lung-deficiency chronic diarrhea, gonorrhea, and leucorrhoea.

*Poria*: *poria*, sweet and light in taste and mild in nature, exerts the curative effect through the heart, lung, spleen, and kidney channels, moisturizes dryness and promotes diuresis, tonifies the spleen, calms the heart, and is used for treatment of edema and oliguria, phlegm-fluid retention, reduced spleen-deficiency appetite, loose stool diarrhea, unease, and palpitation and insomnia.

Chinese date: Chinese date, mild in nature and sweet in taste, exerts the curative effect through the liver and kidney channels, nourishes the livers and kidneys, and replenishes vital essence to improve eyesight, and is used for treatment of consumptive disease and essence deficiency, waist and knee pain, vertigo and tinnitus, internal heat and consumptive thirst, blood deficiency chlorosis, and blurred vision.

The nutritional composition for tonifying spleen of the present disclosure achieves a perfect combination of dietotherapy and medical therapy by scientifically matching the principle of medicinal and edible dual purposes in combination with reasonable traditional Chinese medicines, reflecting the traditional preparing characteristics of the Chinese herbal medicine and providing the prescription based on the theory of the traditional Chinese medical science, and further enriching the purposes of the nutritional composition for tonifying spleen, i.e. regulation, balancing, supplementation, and keeping fit. It has the main efficacy of tonifying the spleen. The above composition can be taken as daily regulation diet.

On the basis of the above examples, the nutritional composition for tonifying spleen further includes a Chinese herbal medicine extract of 1-3 parts, wherein the Chinese herbal medicine extract includes the following components of raw materials in parts by weight: *polygonatum odoratum* 12-30, dried longan pulp 13-24, dried orange peel 7-17, lily 17-26, Chinese yam 13-25, and hyacinth bean 13-28.

*Polygonatum odoratum*: *polygonatum odoratum*, sweet in taste and mild in nature, exerts the curative effect through the lung and stomach channels, nourishes yin and moisturizes the lung, generates the body fluid and nourishes the stomach, and is used for treatment of yin-deficiency dry coughing, polydipsia and dry mouth, and internal heat and consumptive thirst.

Dried longan pulp: dried longan pulp, sweet in taste and warm in nature, exerts the curative effect through the heart and spleen channels, invigorates the heart and spleen, nourishes the blood and soothes the nerves, and is used for treatment of deficiency of qi and blood, palpitation, forgetfulness and insomnia, and blood deficiency chlorosis.

Dried orange peel: dried orange peel, acrid and slightly bitter in taste, and warm in nature, exerts the curative effect through the spleen and lung channels, has the efficacies of regulating qi and middle energizer, drying dampness to reduce phlegm, and can be used for treatment of qi stagnation of spleen and stomach, abdominal fullness and distention, vomit, or chest distress, anorexia, and loose stool caused by retention of damp-turbid substance, but should be used with caution for people with yin and body fluid deficiency and excess heat inside.

Lily: lily, sweet in taste and cold in nature, exerts the curative effect through the heart and lung channels, nourishes yin, moisturizes the lungs, clears away the heart fire, and calms the nerves, and is used for treatment of yin-deficiency dry coughing, overstrained cough and hemoptysis, fidgeting due to deficiency and palpitation, insomnia and dreaminess, and trance.

Chinese yam: Chinese yam, sweet in taste and mild in nature, exerts the curative effect through the spleen, lung, and kidney channels, replenishes the spleens, nourishes the stomach, generates the body fluid, tonifies the lungs, nourishes the kidneys, and astringes essences, and is used for treatment of spleen deficiency, chronic diarrhea, lung deficiency, kidney deficiency, leucorrhoea, and frequent urination.

Hyacinth bean: hyacinth bean, sweet in taste and slightly warm in nature, exerts the curative effect through the spleen, and stomach channels, tonifies the spleen and eliminates dampness, and is used for the treatment of spleen-deficiency diarrhea, leucorrhoea, and summer-heat and dampness vomit and diarrhea.

A small amount of the Chinese herbal medicine extract is added to the nutritional composition for improving the function of tonifying the spleen and removing dampness of the nutritional composition. In the Chinese herbal medicine extract, the Chinese yam is used for replenishing the spleen, nourishing the stomach, generating the body fluid, tonifying the lung, nourishing the kidney, and astringing essences, hyacinth bean is used for nourishing spleen qi to promote healthy transportation, *polygonatum odoratum* and lily are used for nourishing yin to moisturize dryness, generating body fluid and quenching thirst, dried longan pulp is used for invigorating heart and spleen, nourishing the blood and soothing the nerves, and the dried orange peel is used for regulating qi and harmonizing the stomach, so that the various drugs supplement without causing stagnation. The efficacies of tonifying the spleen and removing the dampness are achieved by using various drugs in combination. Moreover, the usage amount of the Chinese herbal medicine extract is relatively small, then it will not destroy the nutritional structure of the original nutritional composition for tonifying spleen, and will not produce an undesirable taste.

As shown in FIG. 1, a method for preparing the nutritional composition for tonifying spleen includes the following steps in sequence:

step 1, preparing raw materials: purifying and sorting rice, soybean, *semen coicis*, *Gorgon euryale* seed, *poria*, and Chinese date for subsequent use, wherein the raw materials are strictly checked, and impurities and soils are removed, effectively reducing the remnant of pollutants such as heavy metals and pesticides;

step 2, frying: frying respective components of raw materials under a condition of 100-200° C. for 25-120 min, wherein the temperature should not be too high to make the starchy food produce acrylamide, thus preventing loss of nutrients;

step 3, dosing: grinding the respective fried raw materials, then mixing and stirring evenly the respective ground raw materials according to proportions to obtain a rice powder, wherein the proportions of the respective raw materials are based on the prescription of the nutritional composition for tonifying spleen of the present disclosure, and in the dosing process, a Chinese herbal medicine extract of 1-3 parts is further added, and the Chinese herbal medicine extract includes the following components of raw materials in parts by weight: *polygonatum odoratum* 12-30, dried longan pulp 13-24, dried orange peel 7-17, lily 17-26, Chinese yam 13-25, and hyacinth bean 13-28. Specifically, the Chinese herbal medicine extract can be prepared through the following method: drying and grinding respective raw materials into a medicinal powder, subjecting the medicinal powder to ultrasonic extraction, centrifugation, and concentration with an ethanol solution of 40-65% in volume percentage to obtain the Chinese herbal medicine extract. In a process of preparing the Chinese herbal medicine extract, a vacuum dryer is used for drying, a temperature parameter is 75° C.-80° C., and a vacuum degree is between a negative pressure of 0.08 MPa and a negative pressure of 0.1 MPa;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 90-120° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 50-60° C.;

step 6: sieving and packaging: sieving the cooled mixed rice grains, and vacuum-packaging the sieved mixed rice grains, wherein the appearance and homogeneity of product particles can be improved by sieving, and in practical operation, after completing the packaging, a product name, a product lot number, specification, net weight, date of manufacture, name of position, and person in charge are recorded and tagged, and a delivery receipt is filled in, then the product is transferred to an intermediate station.

Example 1

A nutritional composition for tonifying spleen includes the following components of raw materials in parts by weight: rice 50, soybean 8, *semen coicis* 2, *Gorgon euryale* seed 3, *poria* 0.4, and Chinese date 0.3.

A preparation method is as follows:

step 1, preparing raw materials: purifying and sorting rice, soybean, *semen coicis*, *Gorgon euryale* seed, *poria*, and Chinese date for subsequent use;

step 2, frying: frying respective components of raw materials under a condition of 100° C. for 120 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 90° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 50° C.;

step 6: sieving and packaging: sieving the cooled mixed rice grains, and vacuum-packaging the sieved mixed rice grains.

Example 2

A nutritional composition for tonifying spleen includes the following components of raw materials in parts by weight: rice 90, soybean 23, *semen coicis* 12, *Gorgon euryale* seed 12, *poria* 1.6, and Chinese date 1.5.

A preparation method is as follows:

step 1, preparing raw materials: purifying and sorting rice, soybean, *semen coicis*, *Gorgon euryale* seed, *poria*, and Chinese date for subsequent use;

step 2, frying: frying respective components of raw materials under a condition of 200° C. for 25 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 120° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 60° C.;

step 6: sieving and packaging: sieving the cooled mixed rice grains, and vacuum-packaging the sieved mixed rice grains.

Example 3

A nutritional composition for tonifying spleen includes the following components of raw materials in parts by weight: rice 60, soybean 10, *semen coicis* 5, *Gorgon euryale* seed 4, *poria* 0.7, and Chinese date 0.6.

A preparation method is as follows:

step 1, preparing raw materials: purifying and sorting rice, soybean, *semen coicis*, *Gorgon euryale* seed, *poria*, and Chinese date for subsequent use;

step 2, frying: frying respective components of raw materials under a condition of 120° C. for 80 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 100° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 58° C.;

step 6: sieving and packaging: sieving the cooled mixed rice grains, and vacuum-packaging the sieved mixed rice grains.

Example 4

A nutritional composition for tonifying spleen includes the following components of raw materials in parts by weight: rice 80, soybean 20, *semen coicis* 9, *Gorgon euryale* seed 8, *poria* 1.3, and Chinese date 1.2.

A preparation method is as follows:

step 1, preparing raw materials: purifying and sorting rice, soybean, *semen coicis*, *Gorgon euryale* seed, *poria*, and Chinese date for subsequent use;

step 2, frying: frying respective components of raw materials under a condition of 130° C. for 60 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 105° C., and 90° C., respectively;

step 5: drying: drying the mixed rice grains through a microwave dryer, wherein a water content of the material is kept below 12%, cooling the dried mixed rice grains at a room temperature, wherein a heating temperature of the microwave dryer is kept at 53° C.;

step 6: sieving and packaging: sieving the cooled mixed rice grains, and vacuum-packaging the sieved mixed rice grains.

Example 5

A nutritional composition for tonifying spleen includes the following components of raw materials in parts by weight: rice 70, soybean 15, *semen coicis* 7, *Gorgon euryale* seed 6, *poria* 1, and Chinese date 1.

A preparation method is as follows:

step 1, preparing raw materials: purifying and sorting rice, soybean, *semen coicis*, *Gorgon euryale* seed, *poria*, and Chinese date for subsequent use;

step 2, frying: frying respective components of raw materials under a condition of 150° C. for 40 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 110° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 55° C.;

step 6: sieving and packaging: sieving the cooled mixed rice grains, and vacuum-packaging the sieved mixed rice grains.

Example 6

A nutritional composition for tonifying spleen includes the following components of raw materials in parts by weight: rice 70, soybean 15, *semen coicis* 7, *Gorgon euryale* seed 6, *poria* 1, Chinese date 1, and a Chinese herbal medicine extract 1. The Chinese herbal medicine extract includes the following components of raw materials in parts by weight: *polygonatum odoratum* 30, dried longan pulp 24, dried orange peel 17, lily 26, Chinese yam 25, and hyacinth bean 28. The Chinese herbal medicine extract is prepared through the following method: drying and grinding respective raw materials into a medicinal powder, subjecting the medicinal powder to ultrasonic extraction, centrifugation, and concentration with an ethanol solution of 65% in volume percentage to obtain the Chinese herbal medicine extract. In a process of preparing the Chinese herbal medicine extract, a vacuum dryer is used for drying, a temperature parameter is 75° C., and a vacuum degree is a negative pressure of 0.08 MPa.

A method for preparing the nutritional composition for tonifying spleen is as follows:

step 1, preparing raw materials: purifying and sorting rice, soybean, *semen coicis, Gorgon euryale* seed, *poria*, and Chinese date for subsequent use;

step 2, frying: frying respective components of raw materials treated in step 1 under a condition of 150° C. for 40 min;

step 3, dosing: grinding the respective fried raw materials, then mixing and stirring evenly the respective ground raw materials with the Chinese herbal medicine extract according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 110° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 55° C.;

step 6: sieving and packaging: sieving the cooled mixed rice grains, and vacuum-packaging the sieved mixed rice grains.

Example 7

A nutritional composition for tonifying spleen includes the following components of raw materials in parts by weight: rice 70, soybean 15, *semen coicis* 7, *Gorgon euryale* seed 6, *poria* 1, Chinese date 1, and a Chinese herbal medicine extract 1. The Chinese herbal medicine extract includes the following components of raw materials in parts by weight: *polygonatum odoratum* 12, dried longan pulp 13, dried orange peel 7, lily 17, Chinese yam 13, and hyacinth bean 13. The Chinese herbal medicine extract is prepared through the following method: drying and grinding respective raw materials into a medicinal powder, subjecting the medicinal powder to ultrasonic extraction, centrifugation, and concentration with an ethanol solution of 40% in volume percentage to obtain the Chinese herbal medicine extract. In a process of preparing the Chinese herbal medicine extract, a vacuum dryer is used for drying, a temperature parameter is 80° C., and a vacuum degree is a negative pressure of 0.1 MPa.

A method for preparing the nutritional composition for tonifying spleen is as follows:

step 1, preparing raw materials: purifying and sorting rice, soybean, *semen coicis, Gorgon euryale* seed, *poria*, and Chinese date for subsequent use;

step 2, frying: frying respective components of raw materials treated in step 1 under a condition of 150° C. for 40 min;

step 3, dosing: grinding the respective fried raw materials, then mixing and stirring evenly the respective ground raw materials with the Chinese herbal medicine extract according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 110° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 55° C.;

step 6: sieving and packaging: sieving the cooled mixed rice grains, and vacuum-packaging the sieved mixed rice grains.

Experiment Example 1: Sensory Evaluation of Eating Quality

Evaluating method: scoring is made in comparison with reference samples according to the odor, appearance structure, palatability, taste, and cold rice texture of the rice, and an overall score is a sum of respective items. Scoring rules are shown in Table 1. Products used for the sensory evaluation of this experiment example are staple foods, numbered as products 1 to 7, obtained by mixing the nutritional compositions for tonifying spleen obtained in Examples 1 to 7 of the present disclosure with rice, respectively, a mixing ratio of rice to the nutritional composition for tonifying spleen being 4:1. Statistical results of the evaluation scores corresponding to the products 1 to 7 are shown in Table 2.

An overall score of less than 50 indicates "very bad", 51-60 "bad", 61-70 "ordinary", 71-80 "relatively good", 81-90 "good", and more than 90 "excellent".

Uncovered matters such as specific operation steps, preparation work, evaluator determination, sample approval, instrument, and appliance should comply with GB/T 15682-2008 Inspection of Grain and Oils-Method for Sensory Evaluation of Paddy or Rice Cooking and Eating Quality.

TABLE 1

Scoring Rules for Sensory Evaluation of Steamed Rice

| First-grade Index Score | Second-grade Index Score | Description of specific properties: score |
|---|---|---|
| Odor 20 | Authenticity and Intensity 20 | Having unique aroma of steamed rice, rich in fragrance: 18~20 |
| | | Having unique aroma of steamed rice, delicate in fragrance of steamed rice: 15~17 |
| | | Having unique aroma of steamed rice, but not obvious in fragrance: 12~14 |
| | | Having no fragrance, but without undesirable odor: |

TABLE 1-continued

Scoring Rules for Sensory Evaluation of Steamed Rice

| First-grade Index Score | Second-grade Index Score | Description of specific properties: score |
|---|---|---|
| Appearance Structure 20 | Color 7 | 7~12<br>Having an undesirable odor: 0~6<br>Bright in color: 6~7<br>Normal in color: 4~5<br>Dull in color: 0~3 |
| | Gloss 8 | Having obvious gloss: 7~8<br>Slightly glossy: 5~6<br>Having no gloss: 0~4 |
| | Integrity of Steamed Rice Grain 5 | Compact steamed rice structure, good integrity of steamed rice grain: 4~5<br>Most of the steamed rice having a compact and complete structure: 3<br>Some steamed rice grains explode: 0~2 |
| Palatability 30 | Viscosity 10 | Smooth, Viscous, not sticky to teeth: 8~10<br>Viscous, basically not sticky to teeth: 6~7<br>Viscous, sticky to teeth; or not viscous: 0~5 |
| | Elasticity 10 | Chewy: 8~10<br>Slightly shewy: 6~7<br>Loose, hard, feeling foreign matters present: 0~5 |
| | Hardness 10 | Neither too hard nor too soft: 8~10<br>Slightly hard or slightly soft: 6~7<br>Very hard or very soft: 0~5 |
| Taste 25 | Authenticity and Persistence 25 | Having relatively strong fragrance and sweet taste when chewed: 22~25<br>Having light fragrance and sweet taste when chewed: 18~21<br>Having no fragrance or sweet taste when chewed, but without undesirable odor: 16~17<br>Having no fragrance or sweet taste when chewed, but having an undesirable odor: 0~15 |
| Cold Steamed Rice Texture 5 | Agglomeration, Viscoelasticity, and Hardness 5 | Relatively loose, relatively good in viscoelasticity, moderate in hardness: 4~5<br>Agglomerated, slightly bad in viscoelasticity, slightly hardened: 2~3<br>Hardened, bad in viscoelasticity, and more rigid: 0~1 |

TABLE 2

Statistical Table of Results of Evaluation Scores of Respective Products

| Group | Overall Score/Score | Evaluation Result |
|---|---|---|
| Product 1 | 94 | Excellent |
| Product 2 | 91 | Excellent |
| Product 3 | 93 | Excellent |
| Product 4 | 93 | Excellent |
| Product 5 | 95 | Excellent |
| Product 6 | 87 | Good |
| Product 7 | 90 | Excellent |

It can be seen from the above test results that all the sensory evaluation results made by respective sensory evaluators on the nutritional compositions for tonifying spleen prepared in Examples 1 to 7 in conjunction with rice are "excellent" and "good". It is indicated that the products of the present disclosure have relatively excellent performances in odor, appearance structure, palatability, taste, and cold rice texture.

Experiment Example 2: Animal Ethology Experiment

The present research is intended to create rat damp-heat syndromes by simulating compound factors (external damp-heat environment, high-glucose and high-fat diet, and pathogenic microorganism) such as external environments and dietary habits of human beings in regions of Guangdong, Guangxi, and Hainan, to observe changes of ethology of rats with damp-heat syndromes, and discuss the intervention effect of the efficacy of removing dampness and tonifying spleen of the nutritional composition of the present disclosure to their behaviors.

1. Test Materials:

The nutritional compositions prepared by the raw materials of Examples 1 to 7 and the preparing method of the present disclosure.

2. Grouping

90 SPF rats, half females and half males, with a body weight of 180-220 g, divided into 9 groups according to a random number table, 10 rats in each group, respectively being a control group, a damp-heat syndrome group (damp-heat group), and test groups (Examples 1 to 7).

3. Experiment Method (1) Control group: fed at 20-28° C. in an environment of relative humidity of 50%-60% with common mixed diet at 8:30 each day.

(2) Damp-heat group: fed with high-glucose and high-fat diet for 10 days, wherein from the $1^{st}$ day to the $8^{th}$ day, the rats were placed in a stimulation environmental chamber for two hours at fixed time each day, the temperature in the chamber was 33 (33±2)° C., and the relative humidity was (75±5)%, from the $9^{th}$ day at 8:30, the rats were administrated by gavage once with *Escherichia coli* according to 2 ml/200 g of body weight, and 24 hours later, the infection was again enhanced once according to 1 ml/200 g of body weight, then the rats were moved out of the chamber to the natural environment.

(3) Test groups, i.e. 7 example groups: subjected to the same treatment as the damp-heat group, but from the $4^{th}$ day, after the rats were moved out of the stimulation environmental chamber to the natural environment for 12 hours, the rats of the 7 example groups were respectively administrated by gavage with the nutritional compositions of Examples 1 to 7 according to 2 g/100 g of body weight, once a day for 7 days in total. The behaviors, symptoms, and physical signs of the animals were observed and recorded every day. Results are shown in Table 3.

TABLE 3

Influences of Medicine on Behaviors, Symptoms, and Physical Signs of Animals

| Group | Behavior | Symptom | Physical Sign |
|---|---|---|---|
| Control Group | Flexible in action, and normal in activity | Normal dieting and drinking, with shaped stool | Clean and glossy fur |
| Damp-heat Group | Tired, drowsy and lazy, and obtuse | Reduced appetite, increased excretion times, with sticky stool. After injection of *escherichia coli*, the body temperature rose. | Fluffy hair without gloss |
| Example 1 | At the beginning, being in a worse state than the Control Group, getting to normal later on | Better than the damp-heat group and worse than the control group in dieting and defecation, and finally getting to normal | Clean and glossy fur |
| Example 2 | At the beginning, being in a worse state than the Control Group, getting to normal later on | Better than the damp-heat group and worse than the control group in dieting and defecation, and finally getting to normal | Clean and glossy fur |
| Example 3 | At the beginning, being in a worse state than the Control Group, getting to normal later on | Better than the damp-heat group and worse than the control group in dieting and defecation, and finally getting to normal | Clean and glossy fur |
| Example 4 | At the beginning, being in a worse state than the Control Group, getting to normal later on | Better than the damp-heat group and worse than the control group in dieting and defecation, and finally getting to normal | Clean and glossy fur |
| Example 5 | At the beginning, being in a worse state than the Control Group, getting to normal later on | Better than the damp-heat group and worse than the control group in dieting and defecation, and finally getting to normal | Clean and glossy fur |
| Example 6 | At the beginning, being in a worse state than the Control Group, getting to normal later on | Better than the damp-heat group and worse than the control group in dieting and defecation, and finally getting to normal | Clean and glossy fur |
| Example 7 | At the beginning, being in a worse state than the Control Group, getting to normal later on | Better than the damp-heat group and worse than the control group in dieting and defecation, and finally getting to normal | Clean and glossy fur |

It can be seen from Table 3 that the rats in the control group had no significant abnormal manifestation. Most of the rats in the damp-heat group showed to be tired, drowsy and lazy, slow in reacting, with fluffy hair, reduced appetite, increased excretion times, and sticky stool over time, which better simulated the spleen-stomach damp-heat syndrome. The rats in the test group, before being administrated by gavage with the nutritional compositions, also showed reduced activity and dieting, and sticky stool, indicating successful modeling; after being administrated with the nutritional compositions, the animals in various groups had increased activities, increased food intake, and gradually got to normal in defecation, and the body temperature was restored to the normal level. Therefore, the present test indicates that the nutritional compositions of the present disclosure have apparent improvement on the symptoms of rat models having the spleen-stomach damp-heat syndrome.

The foregoing only describes preferred examples of the present invention and is not intended to limit the present invention. For a person skilled in the art, various modifications and variations may be made to the present invention. Any modifications, equivalent replacements, improvements, etc., made within the spirit and principle of the present invention, should be covered by the scope of protection of the present invention.

What is claimed is:

1. A nutritional composition for tonifying spleen, comprising the following raw material components and proportions thereof, in parts by weight (pbw): rice 50-90 pbw, soybean 8-23 pbw, *Semen coicis* 2-12 pbw, *Gordon euryale* seed 3-12 pbw, *Poria* 0.4-1.6 pbw, and Chinese date 0.3-1.5 pbw, wherein the composition is a composition prepared by the process comprising the following sequential steps:
   step 1, preparing raw materials: purifying and sorting rice, soybean, *Semen coicis*, *Gordon euryale* seed, *Poria*, and Chinese date for subsequent use;
   step 2, frying: frying the prepared raw materials under a condition of 100-200° C. for 25-120 min;
   step 3, dosing: grinding the fried raw materials, then mixing and stirring evenly the ground materials according to the proportions to obtain a rice powder;

step 4, granulating: extruding the rice powder obtained in step 3 through a double-screw extruder, followed by gelatinization and granulation thereof, to obtain mixed rice grains;

step 5, drying: drying the mixed rice grains through a microwave dryer, wherein a water content of the material is kept below 12%, and cooling the dried mixed rice grains at room temperature; and step 6, sieving and packaging: sieving the cooled mixed rice grains, and optionally vacuum-packaging the sieved mixed rice grains, thereby obtaining the spleen-tonifying nutritional composition.

2. The nutritional composition for tonifying spleen of claim 1, comprising: rice 60-80 pbw, soybean 10-20 pbw, *Semen coicis* 5-9 pbw, *Gordon euryale* seed 4-8 pbw, *Poria* 0.7-1.3 pbw, and Chinese date 0.6-1.2 pbw.

3. The nutritional composition for tonifying spleen of claim 2, further comprising a Chinese herbal medicine extract of 1-3 parts, wherein the Chinese herbal medicine extract comprises the following components of raw materials in parts by weight (pbw): *Polygonatum odoratum* 12-30 pbw, dried longan pulp 13-24 pbw, dried orange peel 7-17 pbw, lily 17-26 pbw, Chinese yam 13-25 pbw, and hyacinth bean 13-28 pbw.

4. The nutritional composition for tonifying spleen of claim 1, comprising: rice 70 pbw, soybean 15 pbw, *Semen coicis* 7 pbw, *Gordon euryale* seed 6 pbw, *Poria* 1 pbw, and Chinese date 1 pbw.

5. The nutritional composition for tonifying spleen of claim 4, further comprising a Chinese herbal medicine extract of 1-3 parts, wherein the Chinese herbal medicine extract comprises the following components of raw materials in parts by weight (pbw): *Polygonatum odoratum* 12-30 pbw, dried longan pulp 13-24 pbw, dried orange peel 7-17 pbw, lily 17-26 pbw, Chinese yam 13-25 pbw, and hyacinth bean 13-28 pbw.

6. The nutritional composition for tonifying spleen of claim 1, further comprising a Chinese herbal medicine extract of 1-3 parts, wherein the Chinese herbal medicine extract comprises the following components of raw materials in parts by weight (pbw): *Polygonatum odoratum* 12-30 pbw, dried longan pulp 13-24 pbw, dried orange peel 7-17 pbw, lily 17-26 pbw, Chinese yam 13-25 pbw, and hyacinth bean 13-28 pbw.

7. A method for preparing a nutritional composition for tonifying spleen of claim 1, wherein the method comprises the following steps in sequence:

step 1, preparing raw materials: purifying and sorting rice, soybean, *Semen coicis, Gordon euryale* seed, *Poria*, and Chinese date for subsequent use;

step 2, frying: frying the prepared raw materials under a condition of 100-200° C. for 25-120 min;

step 3, dosing: grinding the fried raw materials, then mixing and stirring evenly the ground materials according to proportions sufficient to obtain a rice powder;

step 4, granulating: extruding the rice powder obtained in step 3 through a double-screw extruder, followed by gelatinization and granulation thereof, to obtain mixed rice grains;

step 5, drying: drying the mixed rice grains through a microwave dryer, wherein a water content of the material is kept below 12%, and cooling the dried mixed rice grains at room temperature; and step 6, sieving and packaging: sieving the cooled mixed rice grains, and optionally vacuum-packaging the sieved mixed rice grains, thereby obtaining the spleen-tonifying nutritional composition.

8. The method for preparing a nutritional composition for tonifying spleen of claim 7, wherein temperatures of three phases of the double-screw extruder are maintained at 60° C., 90-120° C., and 90° C., respectively.

9. The method for preparing a nutritional composition for tonifying spleen of claim 7, wherein a heating temperature of the microwave dryer is maintained at 50-60° C.

10. The method for preparing a nutritional composition for tonifying spleen of claim 7, wherein in the dosing process of step 3 further comprises adding, in parts by weight of the composition (pbw), a Chinese herbal medicine extract of 1-3 pbw, wherein the Chinese herbal medicine extract comprises the following components of raw materials in parts by weight (pbw): *Polygonatum odoratum* 12-30 pbw, dried longan pulp 13-24 pbw, dried orange peel 7-17 pbw, lily 17-26 pbw, Chinese yam 13-25 pbw, and hyacinth bean 13-28 pbw.

11. The method for preparing a nutritional composition for tonifying spleen of claim 10, wherein the Chinese herbal medicine extract is prepared by:

drying and grinding the respective component raw materials into a medicinal powder, and subjecting the medicinal powder to ultrasonic extraction, centrifugation, and concentration with an ethanol solution of 40-65% in volume percentage, thereby obtaining the Chinese herbal medicine extract.

12. The method for preparing a nutritional composition for tonifying spleen of claim 11, wherein in the process of preparing the Chinese herbal medicine extract, a vacuum dryer is used for drying, the vacuum dryer providing a temperature of 75° C. to 80° C. and a vacuum negative pressure of from 0.08 MPa to a vacuum negative pressure of 0.1 MPa.

13. A method for preparing a nutritional composition for tonifying spleen of claim 2, wherein the method comprises the following steps in sequence:

step 1, preparing raw materials: purifying and sorting rice, soybean, *Semen coicis, Gordon euryale* seed, *Poria*, and Chinese date for subsequent use;

step 2, frying: frying the prepared raw materials under a condition of 100-200° C. for 25-120 min;

step 3, dosing: grinding the fried raw materials, then mixing and stirring evenly the ground materials according to proportions sufficient to obtain a rice powder;

step 4, granulating: extruding the rice powder obtained in step 3 through a double-screw extruder, followed by gelatinization and granulation thereof, to obtain mixed rice grains;

step 5, drying: drying the mixed rice grains through a microwave dryer, wherein a water content of the material is kept below 12%, and cooling the dried mixed rice grains at room temperature; and step 6, sieving and packaging: sieving the cooled mixed rice grains, and optionally vacuum-packaging the sieved mixed rice grains, thereby obtaining the spleen-tonifying nutritional composition.

14. The method for preparing a nutritional composition for tonifying spleen of claim 13, wherein temperatures of three phases of the double-screw extruder are maintained at 60° C., 90-120° C., and 90° C., respectively.

15. The method for preparing a nutritional composition for tonifying spleen of claim 13, wherein a heating temperature of the microwave dryer is maintained at 50-60° C.

16. The method for preparing a nutritional composition for tonifying spleen of claim 13, wherein in a dosing process of the step 3, a Chinese herbal medicine extract of 1-3 parts is further added, and the Chinese herbal medicine extract comprises the following components of raw materials in parts by weight: *polygonatum odoratum* 12-30, dried longan pulp 13-24, dried orange peel 7-17, lily 17-26, Chinese yam 13-25, and hyacinth bean 13-28.

17. The method for preparing a nutritional composition for tonifying spleen of claim 16, wherein the Chinese herbal medicine extract is prepared by:

drying and grinding the respective component raw materials into a medicinal powder, and subjecting the medicinal powder to ultrasonic extraction, centrifugation, and concentration with an ethanol solution of 40-65% in volume percentage, thereby obtaining the Chinese herbal medicine extract.

18. The method for preparing a nutritional composition for tonifying spleen of claim 17, wherein in the process of preparing the Chinese herbal medicine extract, a vacuum dryer is used for drying, the vacuum dryer providing a temperature of 75° C. to 80° C. and a vacuum negative pressure of from 0.08 MPa to a vacuum negative pressure of 0.1 MPa.

19. A method for preparing a nutritional composition for tonifying spleen of claim 4, wherein the method comprises the following steps in sequence:

step 1, preparing raw materials: purifying and sorting rice, soybean, *Semen coicis, Gordon euryale* seed, *Poria*, and Chinese date for subsequent use;

step 2, frying: frying the prepared raw materials under a condition of 100-200° C. for 25-120 min;

step 3, dosing: grinding the fried raw materials, then mixing and stirring evenly the ground materials according to proportions sufficient to obtain a rice powder;

step 4, granulating: extruding the rice powder obtained in step 3 through a double-screw extruder, followed by gelatinization and granulation thereof, to obtain mixed rice grains;

step 5, drying: drying the mixed rice grains through a microwave dryer, wherein a water content of the material is kept below 12%, and cooling the dried mixed rice grains at room temperature; and step 6, sieving and packaging: sieving the cooled mixed rice grains, and optionally vacuum-packaging the sieved mixed rice grains, thereby obtaining the spleen-tonifying nutritional composition.

20. The method for preparing a nutritional composition for tonifying spleen of claim 19, wherein temperatures of three phases of the double-screw extruder are maintained at 60° C., 90-120° C., and 90° C., respectively.

* * * * *